(12) United States Patent
Dagenbach et al.

(10) Patent No.: US 8,888,942 B2
(45) Date of Patent: Nov. 18, 2014

(54) PRODUCTION OF TAPE GOODS HAVING DIAGNOSTIC AID

(75) Inventors: Ralf Dagenbach, Schwetzingen (DE); Ronald Hofstadt, Boehl-Iggelheim (DE); Klaus Lurg, Buerstadt (DE); Stefan Pflaesterer, Weinheim (DE); Wolfgang Schwoebel, Mannheim (DE); Thomas Renz, Stuttgart (DE); Ulf Sprung, Holzmaden (DE); Matthias Lamparter, Metzingen (DE); Eric Voelschow, Mannheim (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 11 days.

(21) Appl. No.: 13/278,965

(22) Filed: Oct. 21, 2011

(65) Prior Publication Data
US 2012/0273112 A1 Nov. 1, 2012

Related U.S. Application Data

(63) Continuation of application No. PCT/EP2010/055273, filed on Apr. 21, 2010.

(30) Foreign Application Priority Data

Apr. 22, 2009 (EP) .................................. 09158518

(51) Int. Cl.
  *B65C 5/02* (2006.01)
  *B31D 1/02* (2006.01)
  *B65C 9/18* (2006.01)
  *B65C 9/42* (2006.01)
  *G01N 35/00* (2006.01)

(52) U.S. Cl.
  CPC . *B65C 9/42* (2013.01); *B31D 1/026* (2013.01); *G01N 35/00009* (2013.01); *B31D 1/021* (2013.01); *B65C 9/188* (2013.01)

USPC ............ 156/235; 156/230; 156/238; 156/285

(58) Field of Classification Search
  CPC .. B44C 1/1712; B44C 1/1716; B41M 7/0027; B65C 9/188; B65C 9/12; B65C 9/14; B65C 9/1803
  USPC .......................... 156/285, 286, 230, 235, 238
  See application file for complete search history.

(56) References Cited

U.S. PATENT DOCUMENTS 2,303,346 A 12/1942 Flood
4,442,836 A 4/1984 Meinecke et al.
(Continued)

FOREIGN PATENT DOCUMENTS

CA 2311496 A1 6/1999
DE 4139924 A1 6/1993
(Continued)

OTHER PUBLICATIONS

"Drive", Wikipedia, p. 1-3, Jul. 26, 2011. http://207.46.192.232/proxy.ashx?a=http%3A%2F%2Fde.wikipedia.org%2Fwiki%2F . . . .

*Primary Examiner* — Christopher Schatz
(74) *Attorney, Agent, or Firm* — Roche Diagnostics Operations, Inc.

(57) ABSTRACT

A method for producing an analysis tape for fluid samples, in particular body fluids, is proposed. In the method, diagnostic auxiliary labels are transferred to a carrier tape, wherein at least one vacuum roller is used for the transfer of the diagnostic auxiliary labels. The diagnostic auxiliary labels are detected on the vacuum roller. At least one tape position of the carrier tape is furthermore detected. The transfer of the auxiliary labels to the carrier tape is effected in accordance with the detected auxiliary labels and the tape position.

17 Claims, 6 Drawing Sheets

(56) References Cited

U.S. PATENT DOCUMENTS

| | | |
|---|---|---|
| 5,024,717 A | 6/1991 | Winter |
| 5,307,988 A | 5/1994 | Focke et al. |
| 5,554,166 A | 9/1996 | Lange et al. |
| 5,846,838 A | 12/1998 | Chandler |
| 6,036,919 A | 3/2000 | Thym et al. |
| 6,191,382 B1 * | 2/2001 | Damikolas ............... 219/121.62 |
| 6,206,071 B1 | 3/2001 | Majkrzak et al. |
| 6,633,740 B2 | 10/2003 | Estabrooks |
| 2002/0162617 A1 | 11/2002 | Kendall, Jr. |
| 2003/0111184 A1 | 6/2003 | Hilt et al. |
| 2006/0002816 A1 | 1/2006 | Zimmer et al. |
| 2006/0144521 A1 | 7/2006 | Esposito et al. |
| 2006/0173380 A1 | 8/2006 | Hoenes et al. |
| 2006/0216817 A1 | 9/2006 | Hoenes et al. |
| 2007/0284049 A1 * | 12/2007 | Ford et al. ..................... 156/541 |
| 2011/0108190 A1 | 5/2011 | Dagenbach et al. |

FOREIGN PATENT DOCUMENTS

| | | |
|---|---|---|
| DE | 10332488 A1 | 2/2005 |
| DE | 10343896 A1 | 4/2005 |
| EP | 0833778 B1 | 1/2002 |
| EP | 1424040 A1 | 6/2004 |
| EP | 1837170 A1 | 9/2007 |
| EP | 1593434 B1 | 7/2008 |
| JP | 03-098842 A | 4/1991 |
| WO | 97/02487 A1 | 1/1997 |
| WO | 98/48695 A1 | 11/1998 |
| WO | 99/03738 A1 | 1/1999 |
| WO | 20041056269 A1 | 7/2004 |
| WO | 2005/107596 A2 | 11/2005 |
| WO | 2006/013045 A1 | 2/2006 |
| WO | 2009/056546 A1 | 5/2009 |

* cited by examiner

PRODUCTION OF TAPE GOODS HAVING DIAGNOSTIC AID

CLAIM OF PRIORITY

The present application is a continuation application based on and claiming priority to International Application No. PCT/EP2010/055273 filed Apr. 21, 2010, which claims priority to European Application No. 09158518.2 filed Apr. 22, 2009, each of which are hereby incorporated herein by reference in their respective entireties.

TECHNICAL FIELD OF THE INVENTION

The present application relates to a method and a device for producing an analysis tape for fluid samples, in particular body fluids, and more particularly to methods and devices for producing a tape product comprising diagnostic aids, for example diagnostic aids for a single use. Diagnostic aids of this type can comprise in particular one or more test fields of a detection chemical for qualitatively and/or quantitatively detecting at least one analyte in the body fluid. Diagnostic aids of this type may also or alternatively comprise lancets for obtaining a fluid sample of a body fluid, such as are used in the context of diabetes diagnostics, for example. Other fields of application and/or other types of diagnostic aids are also conceivable, however.

BACKGROUND

The examinations of blood samples or other samples of body fluids, such as interstitial fluid, for example, enable, in clinical diagnostics, early and reliable identification of pathological states and targeted and astute monitoring of body states. Medical diagnostics generally presupposes that a sample of blood or interstitial fluid is obtained from the patient to be examined. In order to obtain the sample, the skin of the person to be examined can be perforated, for example at the finger pad or the ear lobe, with the aid of a sterile, pointed or sharp lancet in order thus to obtain for example a few microliters of blood or less for analysis. In particular, this method is suitable for an analysis of the sample which is carried out directly after the sample has been obtained. Primarily in the field of so-called "home monitoring", that is to say where medical laypersons themselves carry out simple analyses of blood of interstitial fluid, in particular for diabetics obtaining blood samples on a regular basis, several times a day, to monitor the blood glucose concentration, lancets and associated devices, so-called puncturing aids, are offered. These are described for example in WO-A 98/48695, U.S. Pat. No. 4,442,836, U.S. Pat. No. 5,554,166 or WO 2006/013045 A1, each of which are hereby incorporated herein by reference in their respective entireties.

Self-monitoring of blood sugar levels is a method of diabetes control that is nowadays applied worldwide. Blood sugar devices in the prior art generally have an analysis device into which a test element (for example a test strip or an analysis tape) is introduced. The sample to be analyzed is applied to a test field of the test element and reacts in the test field with one or more reagents, if appropriate, before it is analyzed. Optical, in particular photometric, and electrochemical evaluation of test elements are the most common methods for rapidly determining the concentration of analytes in samples. Analysis systems comprising test elements for sample analysis are generally used in the field of analysis, environmental analysis, and in the field of medical diagnostics.

The prior art discloses various forms of test elements and test devices for the evaluation thereof. By way of example, strip-type test elements can be used, such as are described for example in the documents CA 2311496 A1, U.S. Pat. No. 5,846,838 A, U.S. Pat. No. 6,036,919 A or WO 97/02487, each of which are hereby incorporated herein by reference in their respective entireties. Further multilayered test elements known in the prior art are analysis tapes comprising a multiplicity of test fields which are provided in a cassette in a manner wound up for use in an analysis device. Such cassettes and analysis tapes are described for example in the documents DE 10 332 488 A1, DE 10 343 896 A1, EP 1 424 040 A1, WO 2004/056269 A1 or US 2006/0002816 A1, each of which are hereby incorporated herein by reference in their respective entireties.

Besides analysis tapes comprising test fields, analysis tapes in which lancets are arranged on a carrier tape have also become known in the meantime, wherein the individual lancets, by means of tape transport, can be progressively used and also disposed of again. One example of a system of this type is shown in WO-A 2005/107596, which is hereby incorporated herein by reference in its entirety.

Hereinafter, therefore, an analysis tape is understood to mean generally a tape with any desired type of diagnostic aids, wherein the diagnostic aids can comprise any desired type of diagnostic aids, for example diagnostic test fields with a detection chemical and/or lancets. A tape can be understood to mean, besides a continuous, strip-type element, in principle, generally any desired transport element which is configured such that it is at least in part pliable, deformable or flexible and which can be configured for example also in the form of a chain, a cord, a link chain or a similar continuous carrier.

Various methods are known from the prior art for producing the analysis tapes. These methods have to satisfy numerous stringent requirements since, in the field of medical diagnostics, stringent requirements are made for example of freedom from contamination for the analysis tapes, and also stringent requirements are made of the quality and the reproducibility of the diagnostic aids applied on the analysis tapes. At the same time, however, the analysis tapes have to be produced cost-effectively since medical diagnostics is under constantly increasing cost pressure.

Exemplary disclosures relating to methods and devices for producing analysis tapes and relating to process and devices ancillary thereto include EP 1 593 434 A2, PCT/EP 2008/064614, US 2003/0111184 A1, EP 1 837 170 A1, U.S. Pat. No. 6,633,740 B2, U.S. Pat. No. 5,024,717, U.S. Pat. No. 2,303,346, EP 0 833 778 B1, DE 41 39 924, each of which are hereby incorporated herein by reference in their respective entireties.

However, such various methods and devices do not completely solve the problem of the requirement for cost-effective and at the same time high-precision production of high-quality analysis tapes with a high throughput. Known methods are restricted in terms of their throughput and can typically be used only for tape speeds of less than one meter per minute with an acceptable tolerance during processing. In addition, many of the known methods have high analysis material rejects, which is unacceptable in view of the rising cost pressure.

Therefore, it is an object of the present invention to provide a method and a device for producing a tape product comprising diagnostic aids which avoid the disadvantages of known methods and which can produce high-precision analysis tapes cost-effectively and with a very high throughput.

SUMMARY

This object and others that will be appreciated by a person of ordinary skill in the art have been achieved according to the embodiments of the present invention disclosed herein. In one embodiment, the present invention comprises a method and a device for producing an analysis tape for fluid samples comprising the features of the independent claims. Advantageous developments of the invention, which can be realized individually or in combination, are presented in the dependent claims. The device can be designed in particular for carrying out the proposed method in one or more of the variants described, such that, with regard to possible configurations of the device, reference may be made to the description of the method, and vice-versa.

The method serves for producing an analysis tape for fluid samples, in particular body fluids. The analysis tape is intended to have a diagnostic or therapeutic function and can comprise in particular at least one diagnostic aid for this purpose. In particular, said diagnostic aid can be at least one diagnostic test field with a detection chemical designed for qualitatively and/or quantitatively detecting one or more analytes in the fluid sample. By way of example, the test chemical can change at least one detectable physical and/or chemical property if it comes directly or indirectly into contact with the analyte to be detected. In particular, an optically detectable property (for example a color change and/or a change in a fluorescence property) and/or an electrochemically detectable property can be involved. As an alternative or in addition, the at least one diagnostic aid can furthermore comprise a lancet designed for perforating part of a patient's skin in order to produce a fluid sample. In this case, test fields and detection chemicals known from the prior art (for example in accordance with the prior art described above) and/or lancet types known from the prior art can be used. It is possible to use analysis tapes which comprise exclusively diagnostic test fields and/or exclusively lancets, wherein the test fields and/or lancets can be arranged for example at regular or irregular distances on a carrier tape. However, analysis tapes comprising test fields and lancets which are arranged alternately, for example, are also conceivable. In this way, by way of example, by means of the analysis tape, firstly a blood sample or some other sample of a body fluid can be generated using a lancet, after which this fluid sample can be analyzed for example with the assistance of a test field adjacent to the lancet on the carrier tape.

In the method proposed, diagnostic auxiliary labels are transferred to a carrier tape, wherein at least one vacuum roller is used for the transfer of the diagnostic auxiliary labels. The diagnostic auxiliary labels are detected on the vacuum roller. By way of example, their position and/or orientation can be detected, for example by means of at least one corresponding first sensor. At least one tape position of the carrier tape is furthermore detected, for example by means of at least one corresponding second sensor. The transfer of the auxiliary labels to the carrier tape is effected in accordance with the detected auxiliary labels and the detected tape position. In this case, a transfer in accordance with the detected auxiliary labels and the detected tape position is understood to mean a transfer which is influenced and/or can be influenced, for example with regard to its point in time and/or with regard to the orientation and/or with regard to the positioning of the auxiliary labels, by the detected tape position and the detected auxiliary labels on the vacuum roller. In particular, one or more of the variables point in time of transfer, transfer location and orientation of at least one auxiliary label, during the transfer, can be influenced directly or indirectly by the detected tape position and at least one detected auxiliary label on the vacuum roller. In this case, a tape position can be understood to mean for example an absolute tape position and/or for example a point in time at which a reference mark is detected by a second sensor. A detection of at least one auxiliary label on the vacuum roller can be understood to mean for example an absolute position and/or an absolute orientation of the auxiliary label on the vacuum roller and/or a current angular position of the vacuum roller and/or a point in time at which the auxiliary label (for example a front edge and/or a rear edge of the auxiliary label) is detected by at least one first sensor. By way of example, on the basis of the detected tape position and on the basis of the detected auxiliary label, it is possible to make a prediction about whether the auxiliary label is positioned in a desired position on the carrier tape in the case of the current rotational speed of the vacuum roller and the current tape speed of the carrier tape. If this is not the case, then it is possible to influence, by way of example, the rotational speed and/or the tape speed, for example by means of an open-loop control and/or closed-loop control. Influencing the rotational speed of the vacuum roller can be useful. The prediction can be effected for example by a corresponding algorithm and/or by comparison with one or more desired values and/or curves. The desired values and/or curves can be stored for example in a data processing device, for example by means of one or more electronic tables. By way of example, it is possible to use electronic tables and/or curves in which pairs comprising detected tape positions and detected auxiliary labels are respectively assigned to manipulated variables, for example control parameters, for example rotational speeds and/or accelerations of the vacuum roller.

In contrast to the prior art, therefore, the invention proposes a method in which auxiliary labels, which can comprise diagnostic functional layers and/or lancets, for example, are transferred highly precisely by means of a vacuum roller to the carrier tape, in which both a detection of a tape position of the carrier tape and a detection of the auxiliary labels are effected. By way of example, the transfer can be effected under open-loop control and/or closed-loop control, for example in accordance with a relative or absolute position of the auxiliary labels on the vacuum roller and/or a relative or absolute position of the carrier tape. By way of example, it is possible to identify the diagnostic auxiliary labels as a whole and/or individual constituent parts of said diagnostic auxiliary labels, wherein, by way of example, a position and/or orientation of the diagnostic auxiliary labels on the vacuum roller can be detected, for example by means of at least one corresponding first sensor. By way of example, it is possible to detect one or more position marks of the diagnostic auxiliary labels on the vacuum roller and/or constituent parts of the diagnostic auxiliary labels, such as, for example, individual edges of the diagnostic auxiliary labels, for example a front edge of a diagnostic auxiliary label on the vacuum roller. A position and/or orientation can be identified in this way. An item of information about a current position and/or orientation can be transferred for example from a sensor to a central or decentralized controller. The at least one tape position of the carrier tape can be detected in an analogous manner. By way of example, it is possible to detect position marks on the carrier tape, wherein, by way of example, each desired position of a diagnostic auxiliary label, onto which the diagnostic auxiliary label is intended to be positioned, is assigned at least one position mark on the carrier tape. These position marks can comprise for example color marks (for example white, black or colorful strips, crosses or similar marks) or other types of position marks, which can be detected by at least one second sensor, for example. The at least one item of information about the tape position of the carrier tape can also be communicated for example to the central or decentralized controller. In this way, it is always possible to know exactly a relative position and/or orientation between carrier tape and diagnostic auxiliary label on the vacuum roller.

The diagnostic auxiliary labels can be provided in particular by continuous supply. In particular, the diagnostic auxiliary labels can be provided by supplying a laminate tape comprising at least one laminate carrier tape and at least one diagnostic functional layer, wherein the diagnostic functional layer can be cut in such a way that the diagnostic auxiliary labels arise. The diagnostic functional layer can be chosen in accordance with the configuration of the diagnostic auxiliary labels and/or the diagnostic function thereof and can comprise for example, as will be explained in even greater detail below, a test chemical and/or a lancet. A simultaneous supply of a plurality of types of diagnostic auxiliary labels is also possible, for example by simultaneously supplying a plurality of laminate tapes having different types of diagnostic functional layers.

The diagnostic functional layer is cut in such a way that the diagnostic auxiliary labels arise. Each of said diagnostic auxiliary labels can comprise for example one or more diagnostic aids or constituent parts of one or more diagnostic aids. In principle, known cutting technologies can be used during the process of cutting, such as, for example, mechanical cutting, stamping or laser cutting. Combinations of different known cutting techniques are also possible. In one embodiment, the diagnostic functional layer is cut before the auxiliary labels are transferred to the vacuum roller. By way of example, it is possible to provide a dispensing edge for the diagnostic auxiliary labels, at which the diagnostic auxiliary labels are removed from the laminate tape and transferred to the vacuum roller. The laminate carrier tape without the removed diagnostic auxiliary labels can then be continuously led further and fed to a waste roll, for example. The diagnostic functional layer can then be cut for example before the dispensing edge or before some other manner of transferring the diagnostic auxiliary labels to the vacuum roller. In one embodiment, the diagnostic auxiliary labels are cut at a distance of between about 0.05 m and about 1.0 m, in other embodiments at a distance of between about 0.1 m and about 0.5 m, and in other embodiments at a distance of about 0.3 m, before the auxiliary labels are transferred to the vacuum roller, for example before a dispensing edge. In principle, however, cutting at or after the dispensing edge is also possible.

In one embodiment, the diagnostic functional layer is converted into diagnostic auxiliary labels in a manner substantially free of losses. This means, in particular, that no excess grid arises, rather that the cutting process, apart from cutting losses that may possibly occur, is effected without the formation of waste, for example grids. The diagnostic auxiliary labels can therefore directly adjoin one another.

The diagnostic auxiliary labels can be cut, in particular, as explained above, using a laser cutting process, in particular using at least one $CO_2$ laser. The laser cutting, in particular in combination with the above disclosed distances between the cutting process and the transfer to the vacuum roller, leads to particularly clean production of diagnostic auxiliary labels. It has been found in this context that cutting on the vacuum roller can lead to contaminants in the finished product, up to unacceptable reject rates.

As explained above, the transfer of the diagnostic auxiliary labels, or the transfer thereof to the vacuum roller, may be effected by means of a dispensing edge. In this case, a dispensing edge should be understood to mean a sharp-edged device or a device having a small radius of curvature, around which the laminate tape with the cut auxiliary labels situated thereon is guided, wherein the auxiliary labels cannot follow the small radius of curvature and, accordingly, are removed from the laminate carrier tape and transferred to the vacuum roller. However, some other manner of transfer to the vacuum roller is also possible, in principle. In particular, the transfer can be effected in such a way that the diagnostic auxiliary labels bear with a functional side, that is to say a test chemical side, for example, on the vacuum roller. Instead of a single vacuum roller, it is also possible to use a plurality of vacuum rollers.

In one configuration of the method, the diagnostic auxiliary labels can be supplied to the vacuum roller by means of at least one laminate drive, which drives a laminate tape. By way of example, said drive can comprise one or more drive rolls. Said drive rolls, wherein the drive can also comprise non-driven rolls, can, by way of example, supply the laminate tape from at least one good winding and, after the transfer of the diagnostic auxiliary labels, feed the laminate carrier tape to at least one poor winding.

The diagnostic auxiliary labels can be transferred from the laminate tape to the vacuum roller, wherein the vacuum roller can be driven by at least one vacuum roller drive. It is possible to use at least one first sensor in order to detect a position and/or orientation of at least one of the diagnostic auxiliary labels on the vacuum roller. By way of example, by means of the at least one first sensor, as explained above, it is possible to detect a point in time at which the first sensor detects the diagnostic auxiliary label or a constituent part thereof, for example a front edge and/or a rear edge. As an alternative or in addition, the diagnostic auxiliary label can also be detected in some other way, for example by means of a camera which detects the diagnostic auxiliary label and/or the positioning and/or orientation thereof. In one embodiment, in each case at most exactly one diagnostic auxiliary label is situated on the vacuum roller. The first sensor can comprise for example an optical sensor, for example a reflection sensor and/or an image processing system, which detects the diagnostic auxiliary label and/or a position mark or a characteristic, for example at least one edge, of the diagnostic auxiliary label. By way of example, a camera system and/or an image processing system can be used. As an alternative or in addition, it is also possible to use other sensors, for example image sensors, other types of optical sensors or non-optical sensors or combinations of the stated and/or other types of sensors, for example one or more reflection sensors. As explained above, at least one item of information about the position and/or orientation of the at least one diagnostic auxiliary label on the vacuum roller can be transferred for example to a controller, for example a central or decentralized controller. The controller can comprise for example an open-loop control mechanism and/or a closed-loop control, by which the positioning of the diagnostic auxiliary labels on the carrier tape is subjected to open-loop control and/or closed-loop control. In this case, "open-loop control" is generally understood to mean influencing an operating sequence of a device or process according to a predetermined plan. By way of example, output variables can be set depending on input variables and/or state variables. "Closed-loop control", which is understood here to be a sub-form of open-loop control, is generally understood to mean a process in which, for example continuously or discontinuously, in particular continuously, a controlled variable is detected, compared with a reference variable and influenced in the sense of matching to the reference variable. In terms of apparatus, the process of open-loop control and/or the process of closed-loop control can be implemented for example, as described above, wholly or in part in a central or decentralized controller, which can comprise for example one or more electronic components and/or one or more data processing devices. Furthermore, the controller can comprise one or more control loops, for example likewise in turn implemented by one or more electronic components and/or one or more data processing devices.

The carrier tape can be driven by at least one carrier drive. In this case, too, the carrier drive can comprise for example one or more drive rolls and also, if appropriate, non-driven rolls. The carrier tape can be supplied for example from a supply roll and, after the diagnostic auxiliary labels have been applied, can be fed directly or indirectly to an analysis tape roll, for example.

In this case, at least one second sensor can be used in order, by way of example, to detect at least one reference mark on the carrier tape. As explained above, the second sensor, too, can comprise for example an optical sensor, for example a camera system and/or an image processing system, and/or a more simply designed optical sensor, for example a simple black-white detector, which can detect the at least one reference mark, in particular at least one reflection sensor, in particular a reflection sensor which detects the reflection of a laser beam from the carrier tape. As an alternative or in addition, it is also possible to use non-optical sensors, or combinations of the stated and/or other types of sensors.

The at least one reference mark on the carrier tape can comprise for example reference strips, reference crosses or the like. By way of example, in each case at least one reference mark can be assigned to at least one desired position of a diagnostic auxiliary label on the carrier tape. The reference marks can be printed onto the carrier tape for example in a printing method, for example screen printing, flexographic printing, inkjet printing, pad printing, stencil printing or similar methods.

In one embodiment in which the three drives mentioned are provided, at least the vacuum roller drive and the carrier drive are synchronized. In this case, in the context of the present invention, the term "synchronized" should be understood to mean that the drives are operated in a predetermined or known or adjustable, in particular controllable, drive ratio with respect to one another. In particular, this can mean that the laminate drive and the carrier drive can be operated in a fixed, in particular exactly predeterminable, drive ratio with respect to one another, such that, by way of example, a tape speed of the carrier tape and a tape speed of the laminate tape can be set in a fixed ratio with respect to one another. With regard to the carrier drive and the vacuum roller drive, synchronization can mean, for example, that a drive speed of the vacuum roller can be subjected to open-loop control, in particular to closed-loop control, in order to correctly position the diagnostic auxiliary label in the desired position. This is explained in even greater detail below on the basis of the exemplary embodiments. Other types of synchronization within the meaning of the definition above are also possible however, in principle.

In particular, this can mean that, by way of example, taking account of the position and/or orientation of the at least one diagnostic auxiliary label on the vacuum roller and taking account of the respective position of the at least one reference mark identified, in particular a transfer of the diagnostic auxiliary label to the carrier tape can be effected under open-loop control and/or under closed-loop control. By way of example, a central open-loop controller and/or closed-loop controller can be provided, which comprises at least one open-loop control mechanism and/or at least one closed-loop control, which, taking account of the stated items of information about the position and/or orientation of the at least one diagnostic auxiliary label on the vacuum roller and taking account of the position of the reference mark on the carrier tape, subjects one or both of said drives, that is to say the vacuum roller drive and/or the carrier drive, to open-loop control and/or closed-loop control, such that the diagnostic auxiliary label is transferred to a desired position on the carrier tape. By way of example, said desired position can be calculated from the respective reference mark. In particular, the at least one second sensor can be arranged, in the tape running direction, upstream of a position for transferring the diagnostic auxiliary label to the carrier tape. The desired position can therefore comprise, besides an absolute position on the carrier tape, a position in the generalized sense, for example also a relative positioning time. By way of example, the desired position can be characterized by the fact that the diagnostic auxiliary label, at a predetermined point in time after the reference mark passed the second sensor, has to be transferred to the carrier tape in order for it to be positioned in an absolute desired position on the carrier tape.

In the method proposed, at least one control loop can be used, in particular, which can comprise for example one or more electronic regulators and/or software-controlled regulators. By way of example, said at least one control loop, as explained above, can be contained in a central or decentralized controller of a device for carrying out the method according to the invention, which can comprise one or more electronic components and/or one or more data processing components. The control loop can control the vacuum roller drive and/or the carrier drive taking account of the position and/or the orientation of the diagnostic auxiliary label on the vacuum roller and the position of the reference mark in such a way that the diagnostic auxiliary labels are transferred to the carrier tape in each case in the desired position.

Optionally, the laminate drive can also be synchronized with the vacuum roller drive and the carrier drive. Thus, by way of example, the carrier drive can also be included in said control loop, such that, by way of example, the transfer of diagnostic auxiliary labels to the vacuum roller can also be effected under closed-loop control, such that, by way of example, no accumulation of diagnostic auxiliary labels forms.

The control loop can comprise for example one or more drive regulators, that is to say for example output stages for the closed-loop control and/or open-loop control of one or a plurality or all of the drives, and also, if appropriate, one or more processors. Furthermore, the control loop can comprise the sensors mentioned and also, if appropriate, further sensors. The control loop can be combined physically to form a unit, for example, but also can also be constructed in a decentralized manner. In various embodiments, the control loop may comprises at least one processor, at least two, and possibly even three drive regulators (that is to say amplifiers, output stages for driving the drives) and also the abovementioned at least one first sensor and the at least one second sensor. The at least one processor can be designed for example in terms of program technology to carry out a control program. As an alternative or in addition, however, it is also possible to use electronic components, for example active and/or passive electronic control components.

The control loop can be configured in particular in such a way that it operates the laminate drive in a fixed drive ratio with respect to the carrier drive. In particular, a drive roll of the laminate drive can be operated in a fixed rotation ratio with respect to at least one drive roll of the carrier drive. The fixed drive ratio can correspond in particular to a fixed ratio of a laminate tape speed to a carrier tape speed. By way of example, the lengths of the diagnostic auxiliary labels on the laminate tape as a ratio with respect to the distance between adjacent desired positions of the diagnostic auxiliary labels on the carrier tape after the diagnostic auxiliary labels have been applied should be taken into account here. By way of example, the carrier drive and the laminate drive can be operated in a drive ratio of 1:7. The laminate drive and the carrier drive may be synchronized in such a way that they are strongly coupled by virtue of said drive ratio, for example the drive ratio of 1:7, being fixedly maintained. The control loop can then act in particular exclusively on the vacuum roller drive and control the vacuum roller drive in such a way that the latter is accelerated or decelerated in order to transfer the diagnostic auxiliary labels to the carrier tape in each case exactly in the desired positions. The control loop can therefore be designed in such a way that the carrier drive and the laminate drive are coupled in a fixed drive ratio, whereas the vacuum roller drive is controlled taking account of the signals of the first sensor and of the second sensor in order to transfer the diagnostic auxiliary labels to the carrier tape in the desired positions.

During the calculation of the control loop, which, as described above, can be implemented wholly or partly as software, in particular a so-called virtual axis can be used. A virtual axis should be understood to mean a hypothetical ideal axis to which the calculation of the control loop is referred. Virtual axes of this type are known, in principle, from servo-technology. Thus, it is possible in some embodiment to use a virtual axis, in particular, which coincides with an axis of the carrier drive, for example a drive wheel of the carrier drive. Other configurations of the virtual axis are also possible. All other drives can then be referred to this virtual axis. In this way, by way of example, inaccuracies as a result of inertias of drive rolls or the like can be eliminated during the calculation of the control loop.

As explained above, a plurality of first sensors and/or a plurality of second sensors can also be provided. In particular, the at least one second sensor can be constructed in multipartite fashion and comprise at least one first sub-sensor and at least one second sub-sensor. The first sub-sensor and the second sub-sensor can be designed, in particular, for detecting different types of reference marks on the carrier tape. By way of example, the first sub-sensor can be designed to detect a light, for example white, reference mark and/or the edge thereof, whereas the second sub-sensor can be designed for example to detect a dark, for example black, reference mark and/or the edge thereof on the carrier tape, or vice-versa. Since reference marks can be arranged on the laminate tape for different reasons and since different types of reference marks can be provided, ambiguity can occur during the detection of the reference marks. By using a plurality of second sensors, it is possible to resolve this ambiguity, which is advantageous particularly when a device is started up. Thus, by way of example, a plurality of white reference marks can be provided on the carrier tape, said reference marks being positioned differently. If a white sensor is provided as first sub-sensor and a black sensor as second sensor, then the reference marks can be designed for example in such a way that a machine control of the device recognizes that, if a black reference mark has been identified by the second sub-sensor, the "correct" white reference mark has to follow said black reference mark at a predetermined distance. In this way, the correct reference marks can be unambiguously identified from a plurality of white reference marks, and the ambiguities can be resolved.

As described above, optical sensors, for example, can be used as first sensor and as second sensor, in particular as first and second sub-sensors. Laser sensors may also be used, which detect the reflection of a laser beam, for example, which can change as a result of the reference marks and/or the diagnostic auxiliary labels, for example. Laser sensors generally have a high spatial resolution on account of the high concentration of the laser beam.

The carrier drive can have in particular at least one application roller, that is to say a roller on which the diagnostic auxiliary label is applied to the carrier tape. By way of example, said application roller can be configured in such a way that it is configured as a deflection roll or comprises a deflection roll and is designed to deflect the carrier tape, in which case the carrier tape can be guided for example through a roller gap between the application roller and the vacuum roller. In this way, a positioning of the carrier tape relative to the point of application of the diagnostic auxiliary label can be defined very accurately since, by way of example, the use of the application roller makes it possible to ensure that the carrier tape is under tension at the application point.

As explained above, the diagnostic auxiliary label can have, in principle, at least one element having a diagnostic function, for example a function of taking a blood sample and/or an analysis function. In particular, the diagnostic auxiliary label can comprise at least one of the following diagnostic aids: a diagnostic test field with a test chemical designed to detect one or more analytes in the fluid sample, a lancet designed to perforate part of a patient's skin in order to produce a fluid sample. Other configurations or combinations of the stated and/or other types of diagnostic aids are also possible. In this case, a diagnostic auxiliary label can comprise exactly one diagnostic aid or else a plurality of diagnostic aids, for example a plurality of diagnostic aids of differing or identical type.

As described above, the analysis tape can comprise for example a plurality of diagnostic test fields, which can be arranged alongside one another or one behind another in the tape running direction or else perpendicular to the tape running direction. As an alternative or in addition, the analysis tape can comprise lancets and diagnostic test fields in an alternating fashion.

In this case, the method can in particular also be carried out in such a way that defective diagnostic auxiliary labels are identified and discharged. By way of example, the method can be carried out in such a way that defective regions on the laminate tape are identified from the outset and marked as such. In this case, by way of example, at least one defect marking can be applied on the laminate tape. If a defect marking of this type is identified, then the diagnostic auxiliary labels can be identified for example by a defect sensor, which can identify the defect marking, for example, and they can be discharged for example during the transfer from the laminate tape to the vacuum roller and/or on the vacuum roller and/or during the transfer to the carrier tape. The discharge can be effected for example by means of extraction by suction, for example by means of a corresponding suction device. As an alternative or in addition to the use of defect markings, defective diagnostic auxiliary labels and/or defective regions on the laminate tape can also be identified directly, for example in the region of the transfer of the diagnostic auxiliary labels to the vacuum roller and/or on the vacuum roller and/or during the transfer from the vacuum roller to the carrier tape. This defect identification can for example in turn be effected optically, such that, by way of example, pattern recognition and/or color recognition is used to identify whether the laminate tape and/or the diagnostic auxiliary labels are defective. In this case, by way of example, fluorescence measurements can also be used since, by way of example, test chemicals often have a specific fluorescence behavior. The latter can be used for identifying faults.

In addition to the proposed method in one or more of the configurations proposed, a device for producing an analysis tape for fluid samples, in particular for body fluids, is furthermore proposed. The device can be designed in particular for carrying out a method in one or more of the embodiments described. Accordingly, suitable devices can be provided for carrying out the individual method steps. The device is designed to transfer diagnostic auxiliary labels to a carrier tape. The device has at least one vacuum roller for the transfer of the diagnostic auxiliary labels, and also at least one first sensor for detecting the diagnostic auxiliary labels on the vacuum roller and at least one second sensor for detecting a tape position of the carrier tape. The device is designed to carry out the transfer of the auxiliary labels to the carrier tape in accordance with the detected auxiliary labels and the tape position.

The proposed method and the proposed device in one or more of the embodiments described have numerous advantages over known methods and devices. The principal advantage that can be mentioned is the highly precise positioning of the diagnostic auxiliary labels onto the carrier tape, which leads to a highly precise positioning of the diagnostic auxiliary labels even at very high tape speeds, for example up to about 10 m/min or more.

In the method proposed, as explained above, the laminate tape comprising the laminate carrier tape and the at least one diagnostic functional layer can be used as intermediate product. In this case, the laminate carrier tape, which can comprise for example a paper tape and/or a plastic tape and/or a multilayered carrier tape, generally serves only as transport means of the diagnostic functional layer and can subsequently be disposed of or reused, for example. The diagnostic functional layer is adapted to the type of diagnostic aids to be applied and can comprise for example a multiplicity of lancets and/or at least one detection chemical. In the latter case, the diagnostic functional layer can be configured for example as described in EP 1 593 434 A2 and can comprise for example the test chemical in the form of at least one detection film. In addition, the diagnostic functional layer can comprise further layers, such as adhesive layers, for example, which may be arranged in this case between lancet and/or test chemical and the laminate carrier tape, absorbent covering layers, for example spriting layers and/or hydrophilizing or hydrophobizing impregnations. Further layers, for example sealing layers for lancets or the like, can also be included.

In the present invention, the diagnostic aids can be transferred to the carrier tape by means of the diagnostic auxiliary labels in a roll method, for example in a manner similar to the method described in EP 1 593 434 A2, although with considerably improved precision and considerably increased throughputs. For this purpose, the at least one diagnostic functional layer of the laminate tape, as explained above, can for example firstly be cut in such a way that at least one diagnostic auxiliary label arises. The latter can correspond for example to the test labels in EP 1 593 434 A2 and can be for example a self-adhesive auxiliary label.

In contrast to EP 1 593 434 A2, however, the invention proposes improving the transfer of the diagnostic auxiliary labels to the carrier tape by using at least one vacuum roller. In this case, a vacuum roller is understood to mean a vacuum roller which, for example through one or more suction openings arranged circumferentially on the roller, can suck up an auxiliary label and transport it from the laminate tape to the laminate carrier tape by rotation of the vacuum roller. As explained above, it is also possible to use a plurality of vacuum rollers. In order that the auxiliary labels are subsequently released again and applied to the carrier tape, it is possible to utilize adhesion forces between the auxiliary label and the carrier tape, for example. If self-adhesive diagnostic auxiliary labels are involved, for example, then said adhesion forces may be greater than the suction forces of the vacuum roller, such that the diagnostic auxiliary labels are released from the vacuum roller and applied to the carrier tape.

As an alternative or in addition, however, the vacuum roller can also be configured in such a way that, by way of example, in the region of the circumferential segment of the vacuum roller in which the auxiliary labels are applied to the carrier tape, the suction to which the auxiliary labels are subjected is stopped. This can be done for example by interrupting the application of vacuum to the suction openings in said region, or it is even possible to apply excess pressure in a targeted manner in said circumferential region, for example using compressed air.

Vacuum rollers are known in principle from other fields of technology, in which non-medical products are produced. Thus, by way of example, devices are known which remove a "liner" from labels and applies said labels to products. Vacuum rollers may be used in that case. In other contexts, vacuum rollers designated as transfer cylinders have been used in labeling machines. Therefore, for possible configurations of the vacuum roller in the distinct context of the present invention, reference may be made to these other contexts. See, for example, U.S. Pat. No. 6,206,071 B1 and WO 99/03738, incorporated herein by reference above. Other configurations of the vacuum roller are also conceivable, in principle, and can be used in the context of the present invention.

It has been found in the context of numerous tests that the concept according to the invention of using at least one vacuum roller for the transfer of the auxiliary labels to the carrier tape affords considerable advantages with regard to the precision with which the auxiliary labels are applied. While conventional labeling methods only enable slow tape speeds, it is possible by means of a method according to the invention to achieve tape speeds in the range of tens of meters per minute (for example tape speeds of at least about 20 m/min, at least about 30 or 40 m/min and at least about 55 m/min are possible). Furthermore, labeling rates of up to about 500 labels per minute or more can be obtained, where tolerances in the sub-millimeter range, for example of at most about 0.5 mm, can be achieved. Consequently, by means of the method according to the invention, the throughput is increased, costs are reduced, and at the same time a high quality of the analysis tapes produced is maintained or ensured.

One possible configuration of the method and/or of the device, which has already been described above, comprises synchronization of a plurality of drives, for example of the vacuum roller drive and of the carrier drive and optionally also of the laminate drive. What are suitable for use in the drives are for example electric motors, in particular powerful servomotors, which are configured with high accuracy. Thus, it is possible to use three servomotors, for example, which can be driven via a bus system, for example. A specific high-power SPC, for example, can function as installation controller. On account of the high transport speed of the laminate carrier tape and/or of the carrier tape, the reaction times of the SPC controller should be extremely low. Moreover, the reaction time per cycle should always be of identical length in order to be able to achieve an exact synchronization of the drives in the case of variable speeds, since, by way of example, one millisecond switching time at the speed of approximately 55 m/min means a positioning tolerance of about 1 mm in the direction of travel.

The above-described optional use of a laser as a cutting device, for example of a $CO_2$ laser, leads to a particularly high cutting accuracy, a particularly high cutting speed and little cutting waste of the diagnostic auxiliary labels. Embodiments having a remote arrangement from the point where the diagnostic auxiliary labels are transferred to the vacuum roller leads to the advantages explained above. Thus, in particular, synchronization of the cutting device with a drive of the vacuum roller is not absolutely necessary, although such synchronization can naturally be effected even so. Moreover, the positioning accuracy of the diagnostic auxiliary labels on the carrier tape is not dependent on the cutting accuracy since the result of the cutting process can be monitored by means of the at least one first sensor, by direct monitoring of the diagnostic auxiliary label on the vacuum roller. A positioning accuracy and/or a timing of the cutting process is then no longer of importance or merely of considerably reduced importance.

As explained above and in contrast to known labeling methods, such as the labeling method disclosed in EP 1 593 434 A2, for example, the cutting of the diagnostic auxiliary labels in the method proposed can be carried out in particular in a manner substantially free of losses. In this case, "in a manner substantially free of losses" can be understood to mean a process of cutting in which, apart from the cutting waste resulting from the cutting device (which may typically be in the range of one tenth of a millimeter), no waste arises which, as described in EP 1 593 434 A2, would have to be segregated. Therefore, the diagnostic functional layer can be completely cut up into auxiliary labels. This means a considerable advantage over conventional labeling methods, such as not only the method described in EP 1 593 434 A2, but also for example the labeling method in accordance with U.S. Pat. No. 6,206,071 B1 or other known labeling devices, not only since the segregation in practice can cause considerable technical outlay but since now the cost-intensive diagnostic functional layer can be completely utilized.

Further advantageous configurations and advantages can concern the tape guidance of the laminate tape or of the laminate carrier tape and/or of the carrier tape. Thus, by way of example, for better guidance by means of the drives mentioned, the laminate carrier tape and/or the carrier tape can be charged electrostatically, for example, in order to ensure better adhesion for example on one or more rolls of the drives.

As described above, the method can be configured in particular in such a way that a defect identification and/or a discharge of defective diagnostic auxiliary labels can be effected. Thus, the vacuum roller, as described above, can be utilized in particular for discharging defective diagnostic auxiliary labels and/or defective sections of the diagnostic functional layer from the production process. For this purpose, by way of example, the diagnostic functional layer and/or other regions of the laminate tape can be provided with a defect marking that identifies defective sections of the diagnostic functional layer. These defect markings can be applied for example by virtue of the fact that the device described has a defect identification device and/or a marking device. The defect identification device can be configured for example in such a way that the diagnostic functional layer and/or the laminate tape can be examined for defects optically and/or electrically and/or in some other way. By way of example, it is possible in this way to identify a discoloration of a test chemical and/or an incorrect positioning of lancets on the laminate tape. The defect marking device can be used to correspondingly mark the laminate tape and/or the diagnostic functional layer if defects of this type are identified. Thus, by way of example, defect markings can be printed onto the laminate tape and/or the diagnostic functional layer and/or a differently designed marking of the defects can be effected. By way of example, it is possible to use a test chemical itself by the action of a marking beam, for example of a light beam in particular in the visible and/or ultraviolet spectral range. In this way, by way of example, defective sections of the generally light-sensitive test chemical can be colored in order in this way to identify these sections as defective. As an alternative or in addition, however, as explained above, defect identification can also be effected directly upon or before discharge, for example by means of defect identification directly in the region of the vacuum roller. Various configurations are possible.

The device can furthermore have a detection device in the region of the labeling device, that is to say in the region of the vacuum roller and the transfer of the diagnostic auxiliary labels to the carrier tape, for example in direct proximity to the vacuum roller, said detection device identifying the defect marking and/or the defects in the diagnostic auxiliary labels and/or the diagnostic functional layer. By way of example, said detection device can be an optical and/or electrical detection device, which can be specifically adapted to the defect marking and can thus identify printed-on defect markings and/or discolored regions in the test chemical, for example.

The discharge of defective sections of the diagnostic functional layer and/or defective diagnostic auxiliary labels can be effected, as explained above, at different locations and/or in different ways. The vacuum roller used permits particularly simple discharge of such defective sections of the diagnostic functional layer and/or defective diagnostic auxiliary labels. Thus, diagnostic auxiliary labels and/or sections which have been identified as defective and/or marked as defective before or after application to the vacuum roller can be removed and disposed of, for example. For this removal of defective sections and/or defective diagnostic auxiliary labels, the device can have a withdrawal device, for example, where various devices can be used as withdrawal device. Thus, it is possible to effect the removal of the defective sections at the vacuum roller for example electrostatically, mechanically or in some other way. In one embodiment an extraction device using suction is used, which is utilized for removing the defective sections and which is triggered by the detection device, for example, as soon as a section identified as defective and/or marked as defective and/or such a diagnostic auxiliary label is identified. Such extraction by suction can be effected within fractions of a second, such that the production process as a whole need not be influenced, or need be influenced only to an insignificant extent. Moreover, the extraction device using suction affords the advantage that contaminants can also be removed at the same time as or in addition to defective sections of the diagnostic functional layer, with the result that a problem of contamination can be significantly reduced.

As described above, the diagnostic auxiliary labels can comprise one or more diagnostic aids which are applied to the carrier tape at regular or predetermined distances for example by the method described. In one embodiment, the diagnostic auxiliary labels each comprise a plurality of diagnostic aids of this type, and further may comprise a plurality of identically designed diagnostic aids. In this way, the method described can be rationalized for example by virtue of the diagnostic functional layer of the laminate tape having a plurality of tracks of diagnostic aids arranged in a parallel fashion in a laminate tape running direction, such that, during the process of cutting the diagnostic functional layer, the diagnostic auxiliary label that arises in the process has a plurality of diagnostic aids which are then applied to the carrier tape in an arrangement perpendicular to the carrier tape running direction. The carrier tape can then be cut into a plurality of sub-tapes for example by means of a mechanical or optical cutting process parallel to the direction of longitudinal extent, wherein, by way of example, each of said sub-tapes comprises a diagnostic aid of each diagnostic auxiliary label. The sub-tapes can subsequently be used as actual analysis tapes. This described method of cutting into a plurality of sub-tapes can be configured for example analogously to the cutting method described in EP 1 593 434 A2.

Furthermore, it is pointed out that the analysis tapes can subsequently also be divided into analysis tape sections in the longitudinal direction. In this case, sub-tapes can arise which can be wound into a corresponding tape cassette, for example. Each of said sub-tapes can comprise a plurality of analytical aids. As an alternative, the analysis tapes can also be cut in such a way that they are processed to form test strips which each comprise only one or a plurality of analytical aids. Various configurations are possible.

Furthermore, the method can be developed further by virtue of the carrier tape comprising additional markings. As described above, the tape position of the carrier tape can be detected for example by means of at least one reference mark on the carrier tape, which, by way of example, can be configured as a position mark and/or can comprise at least one position mark. As an alternative or in addition, the carrier tape can comprise further marks, for example further reference marks for an optical calibration of the analysis tape. In particular, it is possible to apply color markings on the carrier tape, which enable a color balancing. These are advantageous particularly when the analysis tape comprises diagnostic aids which are utilized optically, for example test chemicals which are utilized for an optical analyte detection. Thus, the reference marks can comprise for example white and/or black fields which can be utilized for such a color balancing and/or a calibration of light sources used, for example reflectance measurements. In this case, the at least one optional reference mark can also have dual functions and can be utilized for example as a reference mark for an identification of the tape position and as a reference mark for a calibration and/or color balancing. Various configurations are possible.

The method proposed and the device proposed can be distinguished in particular by the fact that the preliminary process of label cutting can be obviated. The cutting of the diagnostic auxiliary labels can be effected for example approximately 30 cm before the point where the labels are transferred to the vacuum roller, which is used as an application roller. As a result, the labels can be cut without a grid, which can lead to a material saving of approximately 25 percent. The diagnostic auxiliary labels can be transferred from said vacuum roller to the carrier tape, which can be configured as a carrier film, for example, which can be guided by way of an application roller, for example. The vacuum roller and the application roller can be equipped with independent drives and synchronized in such a way that the process of application to the carrier film can be effected with a very high accuracy and, in addition, inaccuracies that may be introduced by the feedstock of the carrier film can also be compensated for.

As explained above, this high accuracy can be achieved by means of a highly dynamic control loop, for example. Part of the control loop can be, firstly, the at least one second sensor, which detects the at least one reference mark on the carrier tape, for example, and, secondly, a first sensor, which can identify for example the diagnostic auxiliary labels, for example edges of the respective diagnostic auxiliary labels, after transfer to the vacuum roller on the vacuum roller.

Furthermore, as explained above, a virtual axis can be part of the control loop and can be used to compensate for possible inaccuracies, for example tolerance fluctuations, while the diagnostic auxiliary labels, sucked up on the vacuum roller, move from the point of transfer to the vacuum roller, for example from the apex of the vacuum roller, to the corresponding position on the carrier tape by means of the rotation of the vacuum roller. Therefore, machines equipped with this new method can be operated at much greater path speeds in comparison with machines having the previous method. The limit of the path speed is defined, in principle, by the switching speed of the sensors used. The possibility of synchronizing the various drives with the aid of said highly dynamic control loop and the optional virtual axis particularly distinguishes this new method.

The invention is to be explained in more detail by the following figures and examples.

BRIEF DESCRIPTION OF THE DRAWINGS

The following detailed description of the embodiments of the present invention can be best understood when read in conjunction with the following drawings, where like structure is indicated with like reference numerals and in which.

In order that the present invention may be more readily understood, reference is made to the following detailed descriptions and examples, which are intended to illustrate the present invention, but not limit the scope thereof.

DETAILED DESCRIPTION OF EMBODIMENTS OF THE PRESENT INVENTION

The following descriptions of the embodiments are merely exemplary in nature and are in no way intended to limit the present invention or its application or uses.

Figure 1:
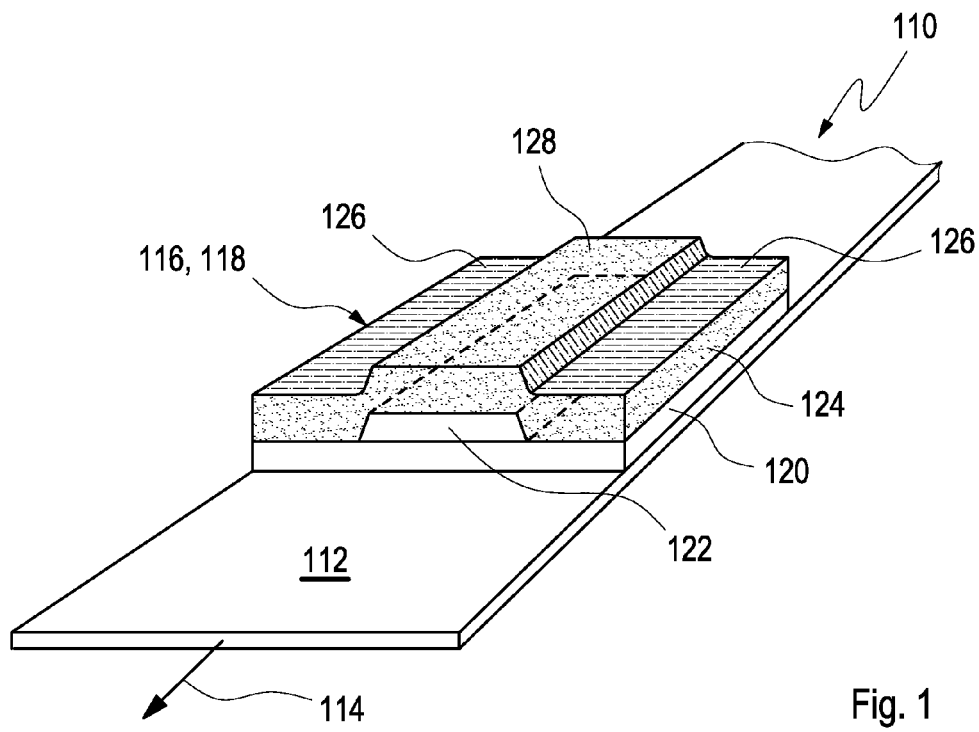
FIG. 1 shows an exemplary embodiment of an analysis tape which can be produced according to a method according to the invention.

FIG. 1 illustrates one possible exemplary embodiment of an analysis tape 110 such as can be produced for example by a method according to the invention described below. The analysis tape 110 comprises a carrier tape 112, which can be configured for example as a carrier film in the form of a plastic film. Said carrier film can be made very thin, for example, with a thickness of between 10 and 15 µm, for example, and can comprise at least one plastic material, for example polyethylene. Other configurations of the carrier tape 112 are also possible, however, for example laminate tapes, paper strips or the like.

A multiplicity of test fields 116 are applied on the carrier tape 112 in a manner spaced apart in a transportation direction 114. In this case, the test fields 116 are each arranged in desired positions on the carrier tape 112. Of these test fields 116, which, by way of example, can be arranged at a distance of 110 mm and can have a length in the transport direction 114 of approximately 15 mm, just one is illustrated in FIG. 1. It should be assumed hereinafter that the test fields 116 are configured for detecting an analyte, in particular blood glucose, in body fluids, in particular in blood.

The analysis tape 110 in accordance with the illustration in FIG. 1 can correspond for example to the exemplary embodiment in accordance with EP 1 593 434 A2. In this exemplary embodiment, the test fields 116 form in each case a diagnostic aid 118 and can be embodied in multilayered fashion for example as self-adhesive test labels. They each comprise a section of an optional adhesive tape 120, of a film of a test chemical 122 and of an optional absorbent covering layer 124 in the form of a fabric. Said covering layer 124 serves to enable an applied liquid sample to be distributed uniformly on the test field 116 and is often also designated as "spriting layer". Outside the test chemical 122, said covering layer 124, which may have hydrophilic properties, is provided in regions with an impregnation 126, which may have hydrophobic properties. By way of example, said impregnation 126 can be a printed-on wax layer which leaves free only a central detection zone 128 in the region of the test chemical 122, within which the liquid sample can spread. The test chemical 122 is intended to be configured to change at least one detectable property, for example an optical or electrochemical property, if it comes into contact with the at least one analyte to be detected. Test chemicals of this type are known from the prior art, for example the prior art cited in the introduction.

Figure 2:
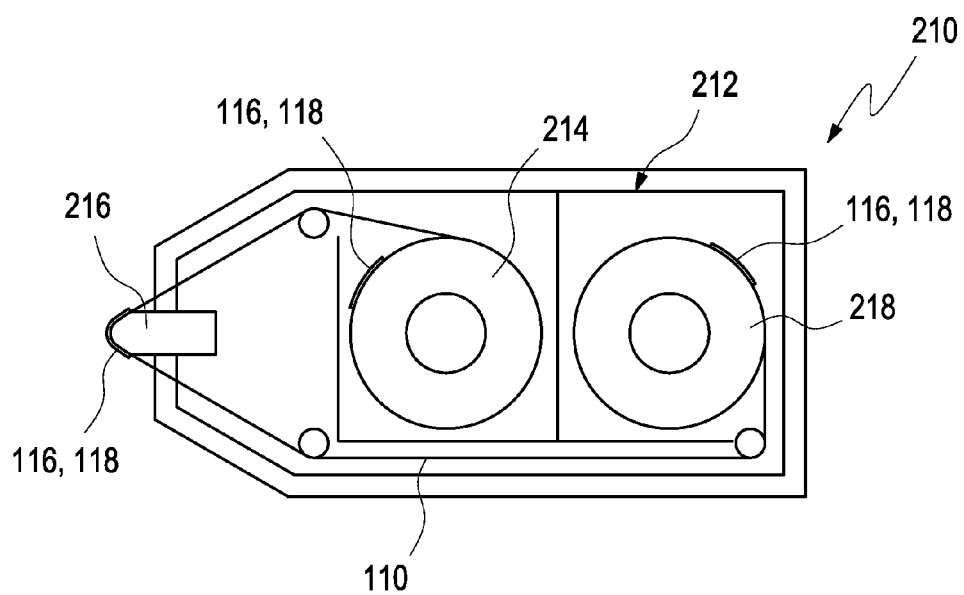
FIG. 2 shows an exemplary embodiment of a blood sugar test device with a tape cassette containing an analysis tape.

FIG. 2 shows, in a highly schematic illustration, a blood sugar test device 210, in which the analysis tape 110, accommodated in a tape cassette 212, can be used. Further optional details of the blood sugar test device 210 are not illustrated in FIG. 2. In this case, the analysis tape 210 is wound on a good winding 214. By means of a process of winding forward, the individual test fields 116 can be exposed in the region of a measuring head 216 in order to apply a blood sugar drop for the determination of glucose. In this case, fluid is taken up in the central detection zone 128 of the covering layer 124, wherein the edge strips provided with the impregnation 126 delimit the spreading of fluid. On account of the multilayered construction, the test fields 116 have a certain height, while the thin, flexible carrier tape 112 in the intervening regions permits reliable sealing at sealing elements, such that secure magazining protected against ambient influences is possible. After use, the test fields 116 that have been used are wound onto a poor winding 218 by the analysis tape 110 being wound further and are thus securely and hygienically remagazined.

Figure 3:
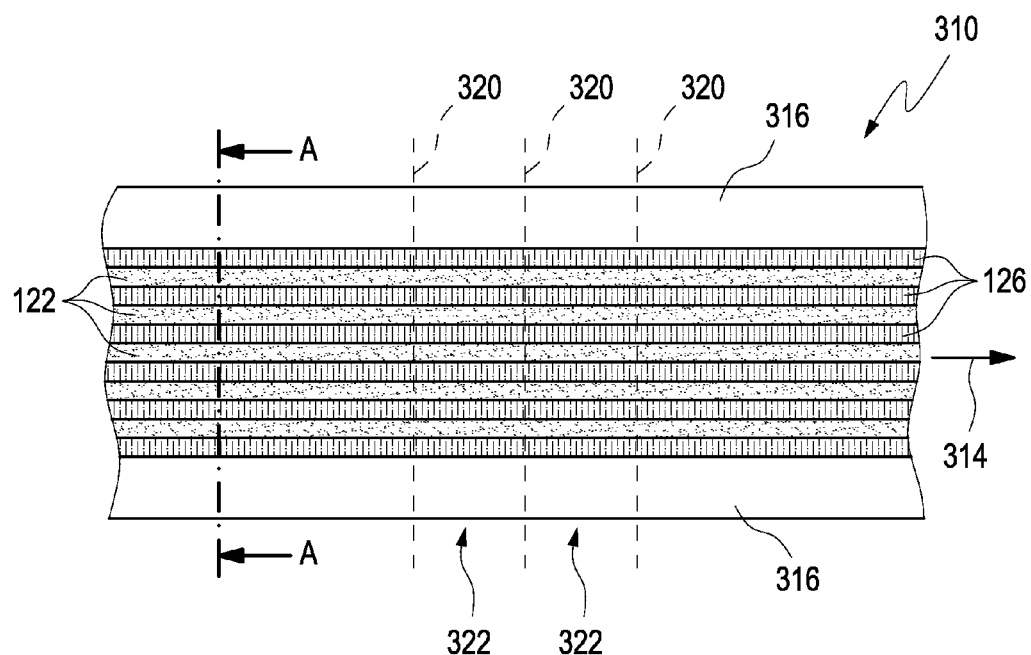
FIG. 3 shows an exemplary embodiment of a laminate tape which can be used in a method according to the invention, in plan view.
Figure 4:
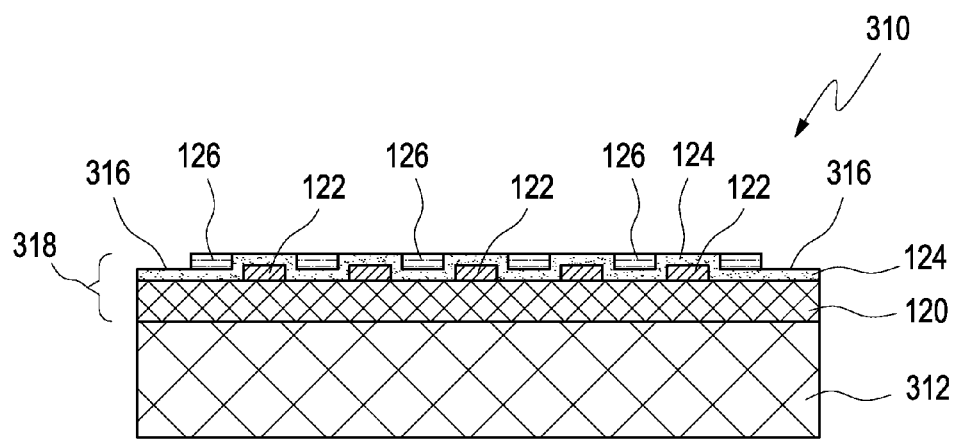
FIG. 4 shows the laminate tape in accordance with FIG. 3 in a sectional illustration.

According to the invention, the production of the analysis tapes 110 may be performed by means of a roll-to-roll method, which is explained in greater detail below by way of example with reference to FIG. 6. Firstly, the carrier tape 112 already described in FIG. 1 is used as a preliminary product for the production of the analysis tape. A laminate tape 310 is used according to the invention as a second preliminary product. By way of example, FIGS. 3 and 4 illustrate such a laminate tape for the production of diagnostic aids 118 with a test chemical 122. In this case, FIG. 3 shows a plan view of the laminate tape 310, whereas FIG. 4 shows a sectional illustration along the sectional line A-A in FIG. 3.

As can be discerned from FIG. 4, the laminate tape has a laminate carrier tape 312. This laminate carrier tape 312 can for example in turn comprise a plastic tape, for example once again a polyethylene film or a similarly designed laminate carrier tape. The adhesive layer 120 is applied to this laminate carrier tape 312, said adhesive layer corresponding to the adhesive layer 120 in FIG. 1 and in one embodiment is concomitantly transferred from the laminate carrier tape 312 to the carrier tape 112 during the method according to the present invention. The test chemical 122 is applied to the adhesive layer in structured tracks, wherein the tracks extend parallel to a running direction 314 of the laminate tape 310. In the present case, these tracks of the test chemical 122 have a width of approximately 2 mm (the illustration in FIGS. 3 and 4 is only schematic and not true to scale) and are arranged equidistantly, with an interspace of likewise approximately 2-3 mm. Overall, five strips of test chemical 122 are provided on the laminate tape 310.

As described above, the test chemical strips 122 are covered with a covering layer 124 of a hydrophilic fabric. This covering is effected in such a way that the covering layer 124 extends over the entire width of the laminate carrier tape 312. As described above, in each case a likewise strip-shaped impregnation 126 is additionally applied to the covering layer 124 outside the test chemical 122, wherein a total of six such strips of the impregnation 126 are applied, which likewise extend in the running direction 314. This application is effected in such a way that edge regions 316 of the laminate tape 310 remain uncovered.

The adhesive layer 120, the test chemical 122, the covering layer 124 and the impregnation 126 together form a diagnostic functional layer 318. In the method described below, this diagnostic functional layer 318 is cut along cutting lines 320 running perpendicularly to the running direction 314, whereas the laminate carrier tape 312 remains uncut. In this way, diagnostic auxiliary labels 322 are formed from the diagnostic functional layer 318 during the cutting process, said diagnostic auxiliary labels being transferred to the carrier tape 112.

Figure 5:
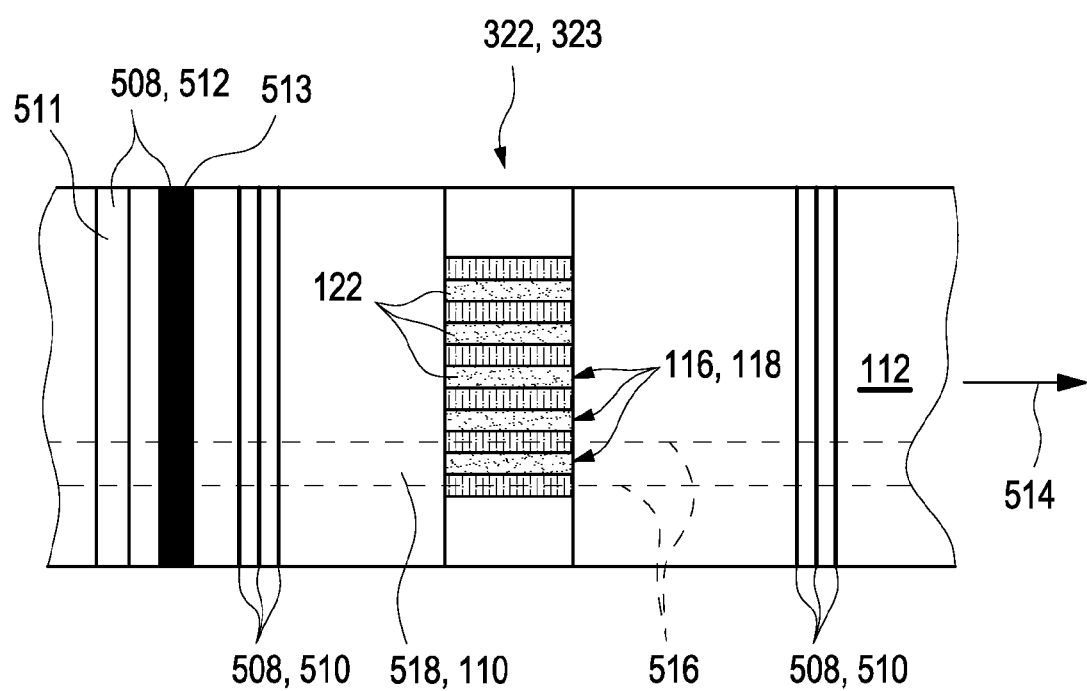
FIG. 5 shows an exemplary embodiment of a carrier tape used in a method according to the invention with an applied diagnostic auxiliary label.

FIG. 5 schematically illustrates such a carrier tape 112 with diagnostic auxiliary labels 322 adhesively bonded thereon. Once again only one diagnostic auxiliary label 322 of this type is shown; other auxiliary labels 322 are arranged equidistantly with respect thereto in each case in desired positions 323. Adjacent desired positions 323 can be arranged for example in each case at a distance of about 110 mm from one another, which can also be designated as "pitch".

Furthermore, it can be discerned in FIG. 5 that a plurality of reference marks 508 having different functions are arranged on the carrier tape 112. By way of example, these reference marks 508 comprise position marks 510 in the example illustrated, said position marks merely being indicated schematically in FIG. 5. These positioning marks 510, can be configured for example as wide strips and can be used for example for the positioning of the test fields 116 in the blood sugar test device 210 in accordance with FIG. 2. Furthermore, these positioning marks 510 can optionally be used in the production method described below. Alongside the positioning marks 510, in the exemplary embodiment illustrated in FIG. 5, the carrier tape 112 comprises in each case color reference marks 512, for example in the form respectively of a white bar 511 applied perpendicularly to the running direction 514 of the carrier tape 112 and a black bar 513, which can be utilized for a color balancing and/or reflectance balancing. These color reference marks 512, too, can be used as reference marks 508 for the production method described in greater detail below.

The diagnostic auxiliary label 322 comprises, in accordance with the strip-type arrangement of the test chemical 122, in this exemplary embodiment five diagnostic aids 118 in the form of test fields 116 which are arranged parallel to one another alongside one another perpendicularly to the running direction 514. In a subsequent cutting method, the carrier tape 112 produced in this way with the diagnostic auxiliary labels 322 applied thereon is cut along cutting lines 516 which run parallel to the running direction 514 and are only indicated in FIG. 5. Overall, in the present case, for example, six cutting lines 516 of this type are necessary, along which the carrier tape 112 with the auxiliary labels 322 applied thereon is cut into sub-tapes 518. Each of these five sub-tapes 518 which arise in this case in FIG. 5 forms an analysis tape 110, for example an analysis tape 110 in accordance with the illustration in FIG. 1. In this way, therefore, five analysis tapes 110 can be produced in parallel and simultaneously by means of the roll-to-roll method according to the invention.

Figure 7:
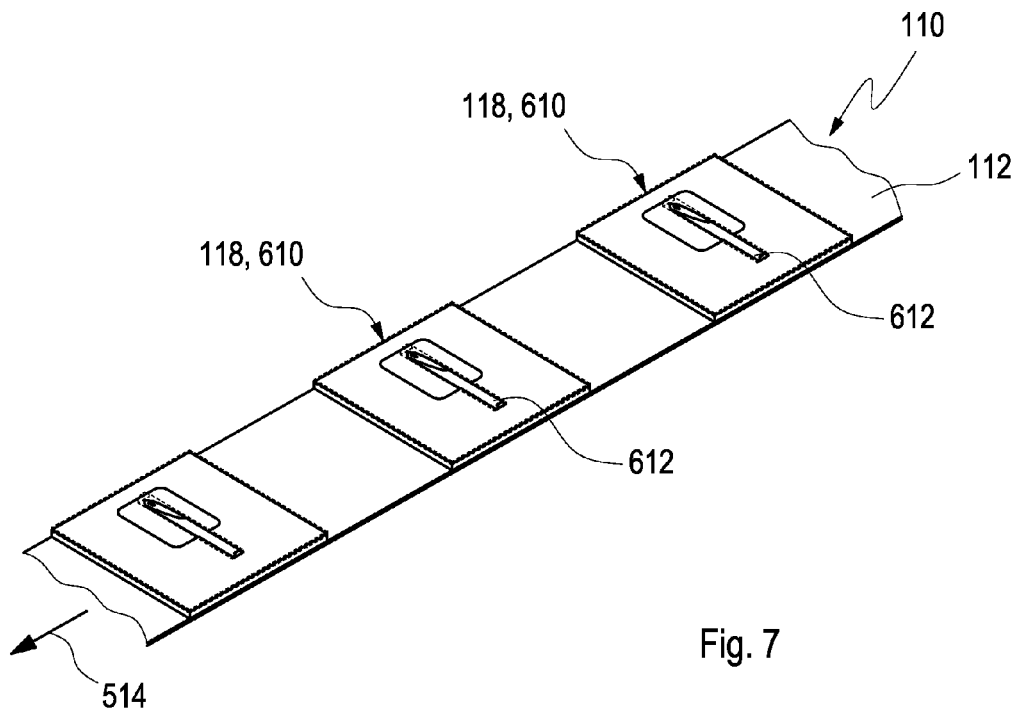
FIG. 7 shows an alternative exemplary embodiment to FIG. 1 of an analysis tape with diagnostic auxiliary elements with lancets.

The exemplary embodiments described above are examples in which the analysis tape 110 exclusively comprises diagnostic aids 118 in the form of test fields 116. However, other types of diagnostic aids 118 are also conceivable and can be used in the context of diagnostics and/or therapeutics in connection with an analysis tape 110. An exemplary embodiment of an alternative analysis tape 110 is illustrated in FIG. 7. This analysis tape 110 once again has a carrier tape 112, to which, in this exemplary embodiment, diagnostic aids 118 in the form of lancet packs 610 each comprising a lancet 612 are applied equidistantly. Reference marks 508, which may be contained on the carrier tape 112 in addition and analogously to FIG. 5, for example, are not illustrated in FIG. 7. The lancet packs 610 are shown in an enlarged detail illustration in FIG. 8. The lancet packs 610, analogously to the diagnostic auxiliary labels 322 in the exemplary embodiments described above, can likewise be fixed in the form of labels on the carrier tape 112. On account of the flexible and flat lancet packs 610, this results in a rollable analysis tape 110 which can be inserted into a handheld device for automatic handling (for example analogously to the handheld device illustrated in FIG. 2).

Figure 8:
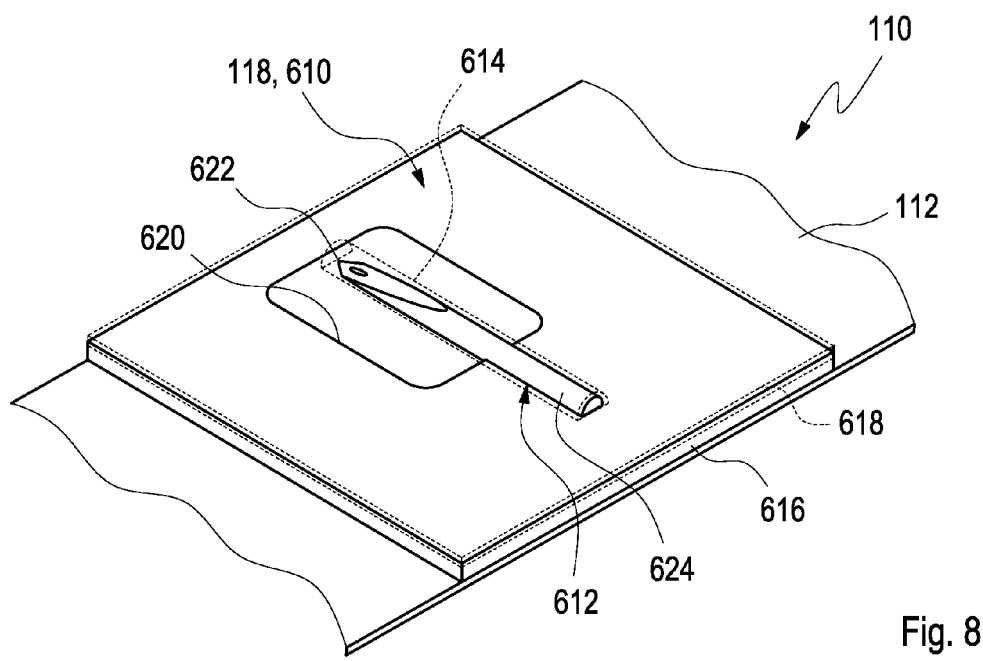
FIG. 8 shows a detail illustration of a diagnostic auxiliary element of the analysis tape in accordance with FIG. 7.

The enlarged view according to FIG. 8 reveals that the respective lancet 612 is protected in a pocket 614 formed by the lancet pack 610. The packet 614 is formed by a film assembly comprising a base film 616 and a covering film 618. An extended pocket region 620 accommodates the lancet tip 622 in a manner lying freely, while a proximal shaft section 624 of the lancet 612 is tightly enclosed. Machine handling even with very small needle elements is thus facilitated, without having to fear damage to the very sensitive lancet tip 622 and impairment of the sterility thereof. A round lancet 613 oriented perpendicularly to the running direction 514 is provided in the embodiment shown. Other orientations and/or shapings are also conceivable, for example in the form of a flat puncturing element provided with a grooved capillary collecting channel.

Figure 9:
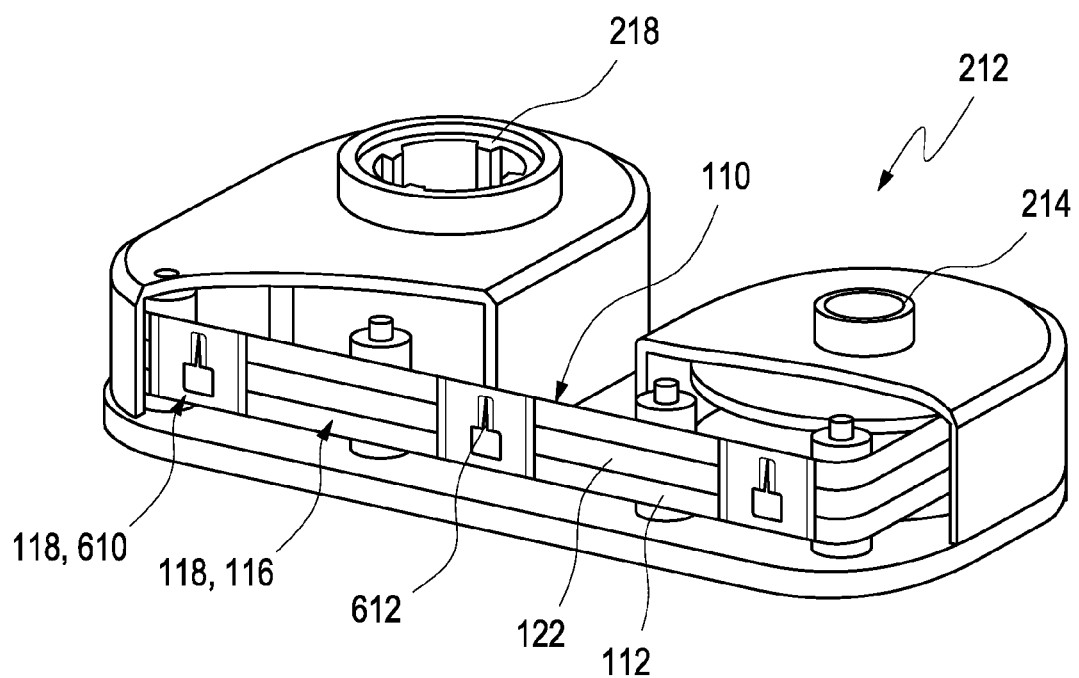
FIG. 9 shows an exemplary embodiment of a tape cassette for a diagnostic test tape on which diagnostic aids with test fields and diagnostic aids with lancets are applied in alternating fashion.

FIG. 9 illustrates an exemplary embodiment of a tape cassette 212 comprising an exemplary embodiment of an analysis tape 110, on which diagnostic aids 118 in the form of test fields 116 and lancet packets 610 are applied in alternating fashion. Each lancet pack 610 comprises a lancet 612, which can be configured as a flat lancet for example in this exemplary embodiment and which, in principle, can be configured similarly to the exemplary embodiment illustrated in FIGS. 7 and 8. Both the test fields 116 and the lancet packs 610 can be applied in the form of labels to a carrier tape 112 of the analysis tape.

The tape cassette 212 once again comprises a good winding 214 as a supply reel for unused tape material and a poor winding 218 as a take-up reel for remagazining or disposal of used diagnostic aids 118. The provision of diagnostic aids 118 can be effected by progressive tape advance, such as in a handheld device, in order to enable a largely automatic measurement sequence. A handheld device of this type can comprise for example an actuator for actuating the lancet 612 respectively situated in an application position, and an evaluation device for evaluating (for example optically evaluating) the measurement of the analyte concentration by means of the respective test field 116 situated in a measurement position. In the course of such a measurement, which can be performed actually by the patient on site, a thin covering film (reference numeral 618 in FIG. 8) is slit open by the lancet 612 and the lancet tip 622 is uncovered in the process. A puncturing movement for example for pricking a finger can then be carried out by means of a suitable actuator. In this case, the proximal shaft section 624 expediently remains connected to the film laminate, thereby simplifying the subsequent disposal of the lancet 612 on the carrier tape 112.

The abovementioned diagnostic aids 118 which can comprise test fields 116 and/or lancets 612 are only some of the many possible exemplary embodiments which can be used for medical diagnostics and/or therapeutics and for which the production method described below can be used. In addition, analysis tapes 110 can be used which can comprise other types of diagnostic aids 118 or combinations of such diagnostic aids 118.

Figure 6:
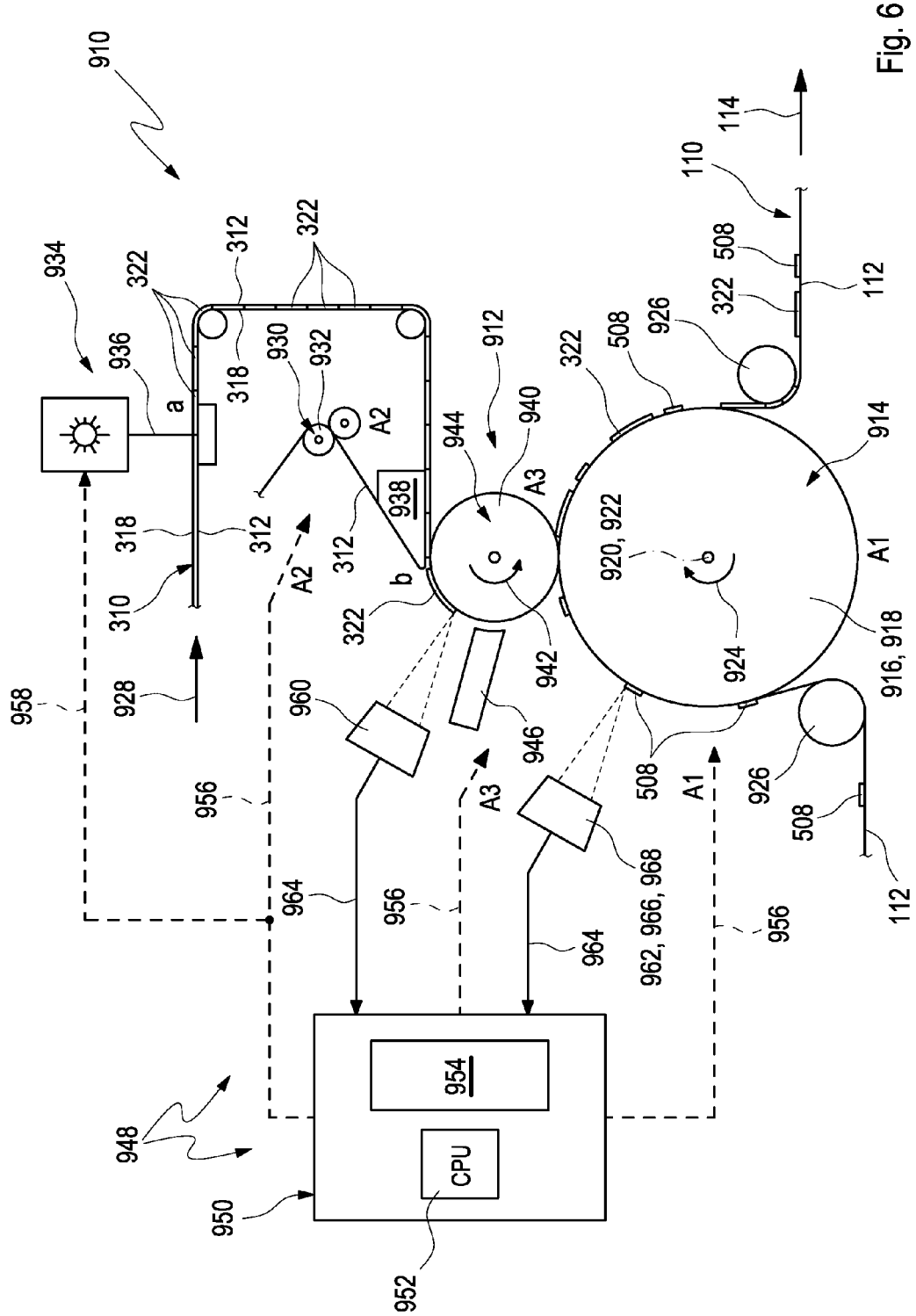
FIG. 6 shows an exemplary embodiment of a device according to the invention for producing an analytical test tape.

FIG. 6 illustrates an exemplary embodiment of a device 910 according to the invention for producing an analysis tape 110. For simplification, it is assumed below that the analysis tape 110 is an analysis tape constructed analogously to the exemplary embodiments in FIGS. 1 and 5. However, in principle, other types of analysis tapes 110 can also be produced by means of the device 910. Furthermore, an exemplary embodiment of a production method according to the invention for producing an analysis tape 110 of this type will be described with reference to FIG. 6.

The device 910 comprises a labeling device 912, by means of which diagnostic auxiliary labels 322 are applied with very high precision to a carrier tape 112 moving in a transport direction 114. With regard to the possible configurations of the carrier tape 112, reference may be made for example to the description above.

The carrier tape 112 is provided by a transport roll, for example, and the carrier tape 112 is driven by a carrier drive 914. By way of example, the carrier tape 112 can move at tape speeds of 55 m/min or even more. The possibility of realizing high tape speeds constitutes one of the essential advantages of the method proposed and of the device 910 proposed.

In the exemplary embodiment illustrated, the carrier drive 914 comprises a drive roll 918 configured as a deflection roll 916. The carrier drive 914, which is designated symbolically by A 1 in FIG. 6, acts, in some embodiments directly, on an axis 920 of said drive roll 918. Said axis 920 coincides with a virtual axis 922 used for the calculation of the control loop, to which virtual axis reference is made with regard to the calculation of all the other drives and the closed-loop control thereof. The drive roll 918 rotates about this axis in a direction of rotation 924. By means of smaller rolls 926, in some embodiments non-driven rolls, it is ensured that the carrier tape 112 bears on the drive roll 918 in the region of the labeling device 912. After passing through the labeling device 912, the carrier tape 112, which is now equipped with the diagnostic auxiliary labels 322 and which has thus become the analysis tape 110 completely or in part (although still further method steps may also follow), can be wound onto a good winding, for example.

Furthermore, in the device 910 according to the invention, a laminate tape 310 is provided in a transport direction 928. By way of example, this provision can be effected from a good winding (likewise not illustrated in FIG. 6). The laminate tape comprises a laminate carrier tape 312 and a diagnostic functional layer 318 and can be constructed for example analogously to the description in FIGS. 3 and 4. The laminate tape 310 is driven by a laminate drive 930, which, by way of example, as illustrated in FIG. 6, can comprise a drive roll 932. The laminate drive 930 is designated symbolically by A2 in FIG. 6. As in the case of the carrier drive 914 as well, a plurality of drive rolls 932 can optionally be provided in the case of the laminate drive 930 as well. After passing through the labeling device 912, the used laminate tape 310, which may now for example consist only of the laminate carrier tape 312, can be fed to a poor winding, for example, which is likewise not illustrated in FIG. 6.

On its way from the good winding to the labeling device 912, the laminate tape 310 passes through a laser cutting device 934 (such as a $CO_2$ laser) or, as an alternative or in addition, some other type of cutting device. The laser cutting device 934 generates a laser beam 936, for example a pulsed or continuous laser beam 936, which, at a cutting location designated by the letter a in FIG. 6, cuts up the diagnostic functional layer 318 of the laminate tape 310, said diagnostic functional layer facing the laser cutting device 934 at this location, at regular distances into diagnostic auxiliary labels 322. These diagnostic auxiliary labels 322 are fed by the laminate drive 930 to a dispensing edge 938 of the labeling device 912. At this dispensing edge 938, the laminate tape 310 is deflected to such a great extent that the diagnostic auxiliary labels 322 are removed from the laminate carrier tape 312 and transferred to a vacuum roller 940 of the labeling device 912. The laminate carrier tape 312 freed of the diagnostic auxiliary labels 322 is subsequently fed to a poor winding, for example, as described above.

One advantage of the arrangement of the cutting device, in particular of the laser cutting device 934, at a distance from the transfer point—designated by the latter b in FIG. 6—from the dispensing edge 938 to the vacuum roller 940 has the effect that laser-abraded residue which may arise during the laser cutting or during other types of cutting processes cannot be transferred to the vacuum roller 940 and contaminate the latter. In one embodiment, the distance between the points a and b in FIG. 6 is at least about 5 cm, in other embodiments at least about 30 cm or more.

The diagnostic auxiliary labels 322 are sucked up by the vacuum roller. The vacuum roller 940 rotates in a direction of rotation 942 opposite to the direction of rotation 924 of the drive roll 918. It should be pointed out, however, that it is also possible to use a plurality of vacuum rollers 940, such that this change in the direction of rotation is not necessarily needed. The vacuum roller 940 is driven by a vacuum roller drive 944. The latter is also designated symbolically by A3 in FIG. 6. From the vacuum roller 940, on the surface of which in each case exactly one diagnostic auxiliary label 322 may be situated, the diagnostic auxiliary labels 322 are transferred to the carrier tape 112 and positioned there in each case in their desired positions on said carrier tape. In this case, the diagnostic auxiliary labels 322 may be applied to the vacuum roller 940 in such a way that they have their adhesive layer (for example reference numeral 120 in FIG. 4) facing upward, that is to say away from the vacuum roller 940.

For the configuration of the vacuum roller 940, reference may be made, in principle, to known vacuum rollers. Thus, the vacuum roller 940 can have a pressure control device, for example, which controls the pressure in suction openings on the surface of the vacuum roller 940 and alternately applies reduced pressure and excess pressure thereto. By way of example, the pressure control device can be coordinated in such a way that vacuum is applied to the diagnostic auxiliary labels between the transfer point at the dispensing edge 938 and the roller gap between the vacuum roller 940 and the drive roll 918 of the carrier drive 914, that is to say the point of transfer to the carrier tape 912, and excess pressure is subsequently applied to said diagnostic auxiliary labels. The pressure control by the pressure control device can thus be configured in such a way that the diagnostic auxiliary labels 322, starting from application in the region of the dispensing edge 938, are sucked up and kept in this state until they reach the roller gap between the drive roll 918—functioning as an application roller—and the vacuum roller 940, at which location the diagnostic auxiliary labels 322 are applied to the carrier tape 912. A pressure reversal may then be effected there by the pressure control device, and an excess pressure can be applied to the suction openings in order to release the diagnostic auxiliary labels 322 and to transfer them to the carrier tape 112.

Possible configurations of the vacuum roller 940 and of the optional pressure control device can be gathered for example from the documents WO 99/03738 and U.S. Pat. No. 6,206,071 B1 already cited. Further exemplary embodiments of a vacuum roller 940 can be gathered for example from the subsequently published international patent application having the application number PCT/EP 2008/064614 from the same company as the applicant of the present patent application.

Furthermore, the device 910 in accordance with FIG. 6 optionally comprises an extraction device 946 using suction. By means of this extraction device 946 using suction, by way of example, at the beginning of the production method, that is to say when the device 910 is started, excess sections of the diagnostic functional layer 318 and/or excess diagnostic auxiliary labels 322 can be extracted by suction. As an alternative or in addition, dirt particles can also be extracted by suction from the surface of the vacuum roller 940, and/or diagnostic auxiliary labels 322 which have been identified as defective and/or marked as defective can be discharged from the method.

As explained above, precision of the labeling device 912 is essential at the high tape running speeds. The device 910 illustrated in FIG. 6 therefore comprises a control loop, which is designated symbolically by the reference numeral 948 in FIG. 6. This control loop 948 comprises a central or decentralized controller 950. In the exemplary embodiment illustrated, the controller 950 comprises at least one data processing device 952, designated here as "CPU", and also 1, 2, 3 or more drive units 954. These drive units 954 can comprise for example individual or combined drive units 954 for the carrier drive 914, the laminate drive 930 and the vacuum roller drive 944. The drive units 954 can comprise amplifier output stages, for example, by means of which for example the rotational speeds of said drives 914, 930 and 944 can be set individually or in groups. The controller 950 is connected to the drives 914, 930, 944 via control lines 956, for example, via which for example signals can be communicated to said drives 914, 930 and 944, such that, by way of example, said rotational speeds can be set precisely.

Furthermore, FIG. 6 illustrates symbolically that the laser cutting device 934 can also be controlled by the control loop 948. In particular, the laser cutting device 934, as likewise illustrated in FIG. 6, can be coupled to the laminate drive 930 directly or indirectly. A laser control line is designated symbolically by the reference number 958 in FIG. 6. It can be coupled to a drive unit 954, for example, which comprises an amplifier output stage for the laminate drive 930. In this way, the laser cutting device 934 can be synchronized for example with the laminate drive 930 in such a way that the length of the diagnostic auxiliary labels 322 always corresponds to the predetermined length.

Furthermore, in the exemplary embodiment in accordance with FIG. 6, the control loop 948 comprises at least one first sensor 960 and at least one second sensor 962. By way of example, as explained above, optical sensors can be involved here. The sensors 960, 962 are connected in each case via sensor signal lines 964 to the controller 950, in particular to the data processing device 952.

The first sensor 960, where it is also possible for a plurality of first sensors 960 of this type to be provided, is arranged in the region of the vacuum roller 940 and detects the diagnostic auxiliary labels 322 on the vacuum roller 940. By way of example, the first sensor 960 can be positioned at a fixed angular position above the vacuum roller 940 and identify a front edge or rear edge of a diagnostic auxiliary label 322 and/or other special features of the diagnostic auxiliary labels 322. By way of example, when such an edge is identified, a signal can be generated and communicated via the associated sensor signal line 964. In this way, by way of example, an item of information about a current position of the diagnostic auxiliary label 322 on the vacuum roller 940 can be generated. As an alternative or in addition to a position, for example an orientation of the diagnostic auxiliary label 322 can also be detected.

The second sensor 962 may be constructed in two parts and in one embodiment comprises at least one first sub-sensor 966 and at least one second sub-sensor 968. The first sub-sensor 966 and the second sub-sensor 968 can be arranged one behind the other for example in the plane of the drawing in FIG. 6, that is to say perpendicular to the direction of longitudinal extent of the carrier tape 112. The second sensor 962 serves for detecting the reference marks 508 or some of these reference marks 508 on the carrier tape 112.

The optional configuration of the second sensor 962 with the two sub-sensors 966, 968 serves, for example, as described above, for resolving ambiguities among the reference marks 508. By way of example, the aim of the second sensor 962 may be to identify a front edge or a rear edge of the white bar 511 of the color reference marks 512. However, further reference marks 508, as explained above, may also be configured wholly or in part in a white color, for example the positioning marks 510. If the second sensor 962 identifies such an edge, therefore, it is unclear what reference mark 508 said edge should be assigned to. In the case of the multipartite configuration of the second sensor 962, by contrast, it is possible for example to configure the first sub-sensor 966 for identifying the white edge. By contrast, the second sub-sensor 968 can be configured for identifying a black edge, for example a front edge and/or a rear edge of the black bar 513 in FIG. 5. If such a black edge is identified, then the data processing device 952 recognizes, on account of its programming, that the "correct" white edge must follow at a predetermined distance from this black edge. In this way, the ambiguity can be resolved and the "correct" white edge can be determined unambiguously. This unambiguity is of importance particularly when the device 910 is started. In principle, however, a different configuration can also be effected.

The control loop 948 may operate according to the following principle. The virtual axis 922 of the drive roll 918 is used as the master axis. All other axes of the drives 914, 930 and 944 may be referred to said virtual axis. This facilitates the conversion and the calculation of the closed-loop control in the data processing device 952, which can in turn control the drive unit 954.

Firstly, the laminate drive 930 is coupled to the carrier drive 914 in a fixed drive ratio. Thus, this coupling can be effected for example in such a way that the transport speed of the carrier tape 112 is 7-fold higher than the transport speed of the laminate tape 310. Other coupling ratios are also possible, in principle. This rigid coupling can be effected for example by a corresponding open-loop control and/or switching of the associated drive units 954.

Furthermore, the signals of the sensors 960 and 962 are taken into account. Thus, a current tape position of the carrier tape 112 is determined by means of the second sensor 962. By contrast, a current position of a diagnostic auxiliary label 322 on the surface of the vacuum roller 940 is determined by means of the first sensor 960. By means of these items of information, including, if appropriate, the known tape speed of the carrier tape 112 and the, if appropriate, known current rotational speed of the vacuum roller 940, it is possible to determine whether the diagnostic auxiliary label 322 would be positioned in its desired position on the carrier tape 112 or in a position deviating therefrom. If a deviation is identified, then the vacuum roller 940 can be correspondingly accelerated or decelerated by the control loop 948, for example by corresponding driving of the associated drive unit 954, such that the desired position is actually achieved. In this way, it is possible to achieve a highly precise positioning of the diagnostic or auxiliary labels 322 in their desired positions even at very high tape running speeds. The use of the virtual axis 922 to which all other axes are referred makes it possible to minimize the errors of the regulator overall. The calculation of the closed-loop control, that is to say for example the calculation of the extent to which the vacuum roller 940 has to be decelerated or accelerated, can be effected wholly or partly in a manner implemented as software. For example in the data processing device 952. As an alternative or in addition, however, the use of hardware-implemented regulators is also possible.

It should be pointed out that the device shown in FIG. 6 merely represents one possible configuration of a device 910 according to the invention. The device 910 can additionally comprise further elements that are not shown in FIG. 6. Thus, by way of example, cutting devices may be provided in order, as described above with reference to FIG. 5, to cut up the analysis tape 110 further into sub-tapes. Moreover, the analysis tape 110 can be cut up into individual strip-type test elements which can be used for example in measuring devices employing individual test strips. In other embodiments, however, tape magazines are used. Furthermore, the device 910 can comprise for example printing devices, devices for applying further layers, test devices, in particular for quality monitoring, marking devices or combinations of the stated and/or other further elements.

Furthermore, it should also be pointed out that the presence of reference marks 508 explicitly defined as such on the carrier tape 112 is not necessarily needed. Thus, by way of example, contours of constituent parts of the carrier tape 112 itself can also be used as reference marks 508 within the meaning of the present invention. By way of example, contours can be applied on the carrier tape 112 as early as before the labeling device 912 is reached, which contours can for example fulfill a separate function and can for example be detected by the second sensor 962. In this case, these contours can be used as reference marks 508 within the meaning of the description above.

The features disclosed in the above description, the claims and the drawings may be important both individually and in any combination with one another for implementing the invention in its various embodiments.

It is noted that terms like "preferably", "commonly", and "typically" are not utilized herein to limit the scope of the claimed invention or to imply that certain features are critical, essential, or even important to the structure or function of the claimed invention. Rather, these terms are merely intended to highlight alternative or additional features that may or may not be utilized in a particular embodiment of the present invention.

For the purposes of describing and defining the present invention it is noted that the term "substantially" is utilized herein to represent the inherent degree of uncertainty that may be attributed to any quantitative comparison, value, measurement, or other representation. The term "substantially" is also utilized herein to represent the degree by which a quantitative representation may vary from a stated reference without resulting in a change in the basic function of the subject matter at issue.

Having described the present invention in detail and by reference to specific embodiments thereof, it will be apparent that modification and variations are possible without departing from the scope of the present invention defined in the appended claims. More specifically, although some aspects of the present invention are identified herein as preferred or particularly advantageous, it is contemplated that the present invention is not necessarily limited to these preferred aspects of the present invention.

What is claimed is:

1. A method of producing an analysis tape for analyzing body fluid samples, the method comprising the steps of:
   transferring diagnostic auxiliary labels from a laminate tape to at least one vacuum roller, wherein the diagnostic auxiliary labels are supplied by means of a laminate drive that drives the laminate tape, and wherein the at least one vacuum roller is driven by at least one vacuum roller drive;
   detecting a position and/or orientation of the diagnostic auxiliary labels on the at least one vacuum roller with at least one first sensor and detecting at least one tape position or reference mark of a carrier tape of the analysis tape with at least one second sensor, wherein the carrier tape is driven by at least one carrier drive, and wherein exactly one diagnostic auxiliary label is situated on the at least one vacuum roller; and
   transferring the diagnostic auxiliary labels from the at least one vacuum roller to the carrier tape in accordance with the detected position and/or orientation of the diagnostic auxiliary labels on the at least one vacuum roller and the tape position or the reference mark of the carrier tape, wherein at least the at least one vacuum roller drive and the at least one carrier drive are synchronized and thus operated in a predetermined, known, adjustable or controllable drive ratio with respect to one another.

2. The method according to claim 1, wherein the diagnostic auxiliary labels are provided by supplying the laminate tape having at least one laminate carrier tape and at least one diagnostic functional layer, wherein the diagnostic functional layer is cut in such a way that the diagnostic auxiliary labels arise.

3. The method according to claim 2, wherein the diagnostic functional layer is cut before the diagnostic auxiliary labels are transferred to the vacuum roller.

4. The method according to claim 2, wherein the diagnostic functional layer of the laminate tape is converted into the diagnostic auxiliary labels in a manner substantially free of losses.

5. The method according to claim 2, wherein the diagnostic auxiliary labels are cut at a distance of between about 0.05 m and about 1.0 m before the diagnostic auxiliary labels are transferred from the laminate tape to the at least one vacuum roller, and wherein the laminate carrier tape remains uncut.

6. The method according to claim 5, wherein the diagnostic auxiliary labels are cut at a distance of between about 0.1 m and about 0.5 m.

7. The method according to claim 6, wherein the diagnostic auxiliary labels are cut at distance of about 0.3 m.

8. The method according to claim 2, wherein the diagnostic auxiliary labels are cut using a laser cutting process.

9. The method according to claim 8, wherein the diagnostic auxiliary labels are cut using a $CO_2$ laser.

10. The method according to claim 1, wherein the diagnostic auxiliary labels are transferred to the at least one vacuum roller at at least one dispensing edge.

11. The method according to claim 1, wherein at least one control loop is used, wherein the at least one vacuum roller drive and the carrier drive taking account of the position and/or the orientation of the diagnostic auxiliary label on the at least one vacuum control loop controls the roller and the position of the reference mark in such a way that the diagnostic auxiliary labels are transferred to the carrier tape in desired positions.

12. The method according to claim 1, wherein a control loop operates the laminate drive in a fixed drive ratio with respect to the at least one carrier drive.

13. The method according to claim 12, wherein the control loop uses a virtual axis, to which a calculation of the control loop is referred, wherein the virtual axis coincides with an axis of the carrier drive.

14. The method according to claim 1, wherein the at least one second sensor comprises at least one first sub-sensor and at least one second sub-sensor, wherein the first sub-sensor and the second sub-sensor are designed to detect different types of reference marks on the carrier tape.

15. The method according to claim 1, further comprising the step of identifying and discharging defective diagnostic auxiliary labels.

16. The method according to claim 12, wherein the fixed drive ratio is about 1:7.

17. The method according to claim 1, wherein the carrier tape moves at a tape speed of about 10 m/min to about 55 m/min.

* * * * *